United States Patent [19]
Anderson et al.

[11] 4,159,289
[45] Jun. 26, 1979

[54] PROCESS FOR PREPARING DIALKYL PHOSPHOROCHLORIDOTHIOATES

[75] Inventors: Alfred P. Anderson, Gonzales; R. Woodrow Wilson; Marshall B. Nelson, both of Baton Rouge, all of La.

[73] Assignee: Ethyl Corporation, Richmond, Va.

[21] Appl. No.: 882,782

[22] Filed: Mar. 2, 1978

[51] Int. Cl.² ............................................. C07F 9/20
[52] U.S. Cl. .................................... 260/990; 260/986
[58] Field of Search ............................... 260/986, 990

[56] References Cited
U.S. PATENT DOCUMENTS

| | | |
|---|---|---|
| 2,868,700 | 1/1959 | Brown et al. ............... 260/429 CY |
| 3,356,774 | 12/1967 | Niermann et al. ............... 260/981 |
| 3,502,750 | 3/1970 | Anglaret et al. ............... 260/986 |
| 3,836,610 | 9/1974 | Diveley ............... 260/986 |
| 3,856,898 | 12/1974 | Diveley ............... 260/990 |

*Primary Examiner*—Alan L. Rotman
*Assistant Examiner*—Robert C. Whittenbaugh
*Attorney, Agent, or Firm*—Donald L. Johnson; John F. Sieberth; James M. Pelton

[57] ABSTRACT

An improved process for the preparation of O,O-dialkyl phosphorochloridothioates in which distillation to recover substantially pure product is carried out in presence of a solubilizing or suspending agent, for example, liquid hydrocarbons, particularly aromatics having at least 10 carbon atoms which have good sulfur solubility, higher boiling point than the product and are inexpensive; specifically, naphthalenes are useful.

7 Claims, No Drawings

PROCESS FOR PREPARING DIALKYL PHOSPHOROCHLORIDOTHIOATES

BACKGROUND OF THE INVENTION

This invention relates to a process for treatment and separation of a mixture comprising O,O-di($C_1$-$C_8$-alkyl) phosphorochloridothioates and sulfur. The O,O-dialkyl phosphorochloridothioates are valuable intermediates, for instance, in the preparation of insecticides. For instance, O,O-diethyl thiophosphoryl chloride is an intermediate in the synthesis of insecticide known as parathion, and O,O-dimethyl thiophosphoryl chloride is an intermediate in the synthesis of the insecticide called methyl parathion.

Several methods have been used for the synthesis of the esters of phosphorochloridothioic acid including one-step and two-step methods. In the one-step process, phosphorus pentasulfide, alcohol and chlorine are reacted to prepare the ester corresponding to the alcohol and then the solvent is removed and the product distilled.

In the two-step process, the first process step reacts phosphorus pentasulfide with an alcohol, such as ethanol, so as to form O,O-diethyl dithiophosphoric acid and hydrogen sulfide, and in a second process step the isolated O,O-diethyl dithiophosphoric acid is chlorinated in an appropriate solvent with chlorine gas, resulting in the formation of O,O-diethyl thiophosphoric acid chloride. Conventionally, the alkyl groups in the dialkyl phosphorochloridothioates have from 1 to 8 carbon atoms and are generally selected from methyl, ethyl, isopropyl, butyl, sec.-butyl, t-butyl, and the like, up through n-octyl and isomers thereof. However, each of these conventional one-step and two-step processes produces sulfur in some form which must be separated from the product. Several solutions to the sulfur problem have been proposed in the prior art. In one process, the product is simply distilled under reduced pressure from the reaction vessel. The sump temperature increases to about 150° during distillation, and upon cooling after terminating distillation the liquid sump phase solidifies and consists essentially of elementary sulfur (confer U.S. Pat. No. 3,356,774).

In another prior art patent disclosing a one-step process, the reaction mixture is treated with hydrogen sulfide to convert the sulfur monochloride formed during the reaction of chlorine with the dialkyl dithiophosphoric acid. When the hydrogen sulfide treatment is carried out at relatively low temperature, a precipitate of sulfur is obtained with practically no by-products. Then, by distilling under vacuum and washing the distillate with water, the diesters of phosphorochloridothioic acid are obtained in very high yield and very high degree of purity (U.S. Pat. No. 3,502,750). In another prior art process using a two-stage chlorination reaction technique, the reaction mixture is chlorinated and then established and maintained at a temperature in the range of 85°–110° C. until it is substantially free of sulfur monochloride and the relatively thermal unstable sulfur that forms becomes more thermally stable so that the product dialkyl thiophosphoryl chloride can be readily and safely removed from the mixture thereof with sulfur by distillation (U.S. Pat. No. 3,836,610). Also, the chlorination-heat treating process can be conducted in a two-stage operation employing first a high temperature to solubilize sulfur, followed by a low temperature to precipitate sulfur from solution. After the high temperature range is established and maintained so that sulfur monochloride is changed to a thermally stable condition, preferably to sulfur and the sulfur goes into solution without substantial decomposition of the phosphoridothioates, the resulting solution is then established at a temperature at which the dissolved sulfur crystallizes, precipitates from solution and is then separated from the solution by settlement, e.g., using filtration, decantation, centrifugation and the like (U.S. Pat. No. 3,856,898).

However, in all of these processes, whether by distillation or by solid/liquid separation, small amounts of free sulfur still remain with the product. Such small amounts affect product purity and have adverse effects on subsequent reactions or may not provide products which meet commercial specifications for production of commercial insecticides. Further, the handling of solid sulfur residues remaining in the reaction vessel is extremely difficult. Batch distillation processes are required because the amounts of sulfur remaining tend to solidify and plug continuous distillation columns. Finally, product losses from the batch vacuum and steam distillation processes are higher than one would like to incur.

THE INVENTION

In order to avoid the disadvantages of the conventional prior art processes, the present invention has been discovered. Accordingly, it is an object of the present invention to avoid problems of residual sulfur in the distillation feed, to avoid batch distillation and to operate without sulfur precipitation causing problems in the continuous distillation columns.

In accord with these and other objects which will become apparent from the description of the invention, the present invention provides an improved process for preparing a dialkyl chloridothioate compound in which phosphorus pentasulfide reacts with an alcohol selected from saturated alkyl alcohols having from one to about 8 carbon atoms, chlorinating the reaction product to produce the corresponding dialkyl phosphorochloridothioate compound, treating the dialkyl phosphorochloridothioate to convert the sulfur monochloride by-product formed to free sulfur and separating a substantial amount of the sulfur from the reaction mixture, the improvement comprising distilling said dialkyl phosphorochloridothioate in the presence of from about 0.1 to about 1 parts per part of said dialkyl phosphorochloridothioate compound of a hydrocarbon liquid containing aromatic hydrocarbon compounds having at least 10 carbon atoms.

In general, the process of the present invention proceeds initially as in any of the hereinabove described prior art patents until the step of separation of the product dialkyl phosphorochloridothioate from the reaction mixture after chlorination or sulfur treatment. Accordingly, each of the above-mentioned patents contains valuable process information which can be employed in the process of this invention and is incorporated herein by reference as if fully set forth. The advantage obtained in the improved process of this invention is that the addition of a material less volatile than the product dialkyl phosphorochloridothioate allows the use of a continuous column distillation system and provides a bottoms stream which contains all of the waste materials in a fluid or suspended state, allowing the product to be recovered from the overhead system and the waste stream to be easily removed for treatment or recycle.

Thus, any lower-boiling impurities are easily removed from the product, a fraction is obtained containing the product and any higher-boiling impurities, as well as the sulfur-solubilizing agent, are removed along with the residual sulfur and sent to waste treatment or solubilizing agent recovery. More specifically, the crude product mixture from the chlorination and/or sulfur treatment steps normally contains large quantities of dialkyl phosphorochloridothioate product and impurities such as organic polymer, sulfur and non-volatile salts which remain suspended. Particularly, sulfur remains suspended in the high-boiling liquid and is preferably dissolved therein.

The present recovery process is particularly desirable because of the essentially complete recovery of the desired product. The polymeric, sulfur and non-volatile impurities are maintained at a sufficiently fluid state that they are normally dissolved or suspended in the high-boiling aromatic hydrocarbon liquid forming a fairly homogeneous phase. Under these conditions, the impurities can be readily removed from the column bottoms with the waste stream, leaving the column reboilers clean and the waste stream in an easily handled, pumpable form. Further, the waste stream is in a form which can be easily handled for efficient disposal or for treatment to recover valuable components such as the high-boiling aromatic hydrocarbon liquid. This latter material can be recycled to the distillation process or burned for fuel value. The following are typical examples of the present invention which are presented for the purpose of illustrating the beneficial characteristics of the improved process. All units in the following examples are given in parts by weight.

EXAMPLE 1

A crude diethyl phosphorochloridothioate material containing about 5 weight percent sulfur and about 20 weight percent of a mixed naphthalenic oil was fed to a 25 tray Oldershaw column having a one-inch diameter. The column was operated at 10 mm Hg absolute overhead pressure, an overhead temperature of 78° C. and a bottoms temperature of 145° C. A reflux ratio of 1:1 was used. Good quality diethyl phosphorochloridothioate was recovered from the overhead condenser and the bottoms stream contained only 4–5 weight percent of diethyl phosphorochloridothioate.

EXAMPLE 2

A crude mixture containing about 76 weight percent diethyl phosphorochloridothioate, 4 weight percent sulfur and 20 weight percent of a mixed naphthalenic oil was fed to a packed glass distillation column 12 feet in height and 4 inches in diameter. The column was operated at 15 mm Hg absolute overhead pressure, overhead temperature of 85° C. and bottoms temperature of 128° C. The reflux ratio was 1:1. At these conditions there was recovered approximately 95 weight percent of the diethyl phosphorochloridothioate fed to the column and no detectable sulfur in the product.

COMPARATIVE EXAMPLE

A crude diethyl phosphorochloridothioate, weighing 223.2 g and containing some solid sulfur, was distilled at a pressure of 20 mm Hg by simple take-over distillation at a pot temperature of 96°–120° C. and head temperature of 91°–102° C. The pale yellow distillate weighed 149.5 g and had the following vapor phase analysis with the results given as percent by weight.

| Component | Percent |
|---|---|
| (EtO)$_2$POCl* | 1.7 |
| (EtO)$_2$PSCl | 92.3 |
| (EtO)$_3$PS | 0.1 |

*Believed but not certain.

The distilled yield was 73.2%.

Preferred operating conditions for continuous column distillation are set by the boiling point of the product dialkyl phosphorochloridothioate at the reduced pressure. For example, overhead temperatures at 15 mm Hg would be 85° C. for diethyl phosphorochloridothioate and 64° C. for dimethyl phosphorochloridothioate; while typical bottoms temperatures are 124°–132° C. and 104°–113° C. for diethyl and dimethyl phosphorochloridothioate, respectively.

The amount of sulfur solubilizing agent used is at least 10 weight percent based on the amount of dialkyl phosphorochloridothioate. The upper limit is limited only by economics and good engineering practice since the greater the amount of sulfur solubilizing agent used the higher the raw materials cost, processing time and waste disposal or recovery problems. It is only sufficient to have enough of the agent to keep the sulfur from forming a separate solid phase which will foul the process equipment at slightly cooler spots in pump lines, flow meters, column feed trays and the like. Use of such a sulfur solubilizing mixture provides an additional advantage in that the resultant stream is more dilute which makes the sulfur less likely to give up large quantities of heat sufficient to cause an explosion with resulting damage to equipment, loss of material, and possible injury to personnel.

From the above examples, it can be seen that the addition of a high boiling water-immiscible hydrocarbon liquid or sulfur solubilizing agent can be employed advantageously in the process of this invention to aid in the separation of dialkyl phosphorochloridothioates from the reaction mixture used in their preparation.

A wide variety of high boiling water immiscible hydrocarbon liquids can be employed in the process of this invention selected from the group consisting of hydrocarbons, particularly aromatic hydrocarbons, having at least 10 carbon atoms and usually not greater than 30 carbon atoms and certain ethers and esters, such as are listed below. The aromatic hydrocarbons are by far the most preferred due to the unexpected fluidity of the distillate residue in these liquids and due to their low cost and availability as by-products, particularly from the petroleum refining industry. The most desirable aromatic hydrocarbons are the naphthalene type, particularly the alkylated napthalenes, either as pure compounds or as mixtures with benzene derivatives or anthracene derivatives. Typical examples of suitable aromatic hydrocarbons are diisopropyl benzene, triisopropyl benzene, tributyl benzene, diphenyl, terphenyl, naphthalene, methylated naphthalenes, either mono- or polysubstituted anthracene, including the alkyl derivatives of anthracene such as the mono-, di- or higher methyl substituted anthracene, ethyl anthracenes, dibutyl anthracenes, and the like. Thus, the sulfur solubilizing agent is preferably a naphthalenic material such as methylnaphthalene or mixtures high in naphthalenics such as coal-tar fractions having a boiling point above that of the product at column pressures, generally above about 100° C. at 15 mm Hg. In some cases, aromatic hydrocarbons which contain other substitutions, such as halogen substitutions, act similarly to hydrocarbons and can be considered equivalents. Examples of these are the chlorinated benzenes and naphthalenes. Other hydrocarbons suitable for use in this invention are dodecane, pentadecane, octadecane, octacosane and the like.

The particular high boiling liquid to be preferred in this invention depends somewhat on the product to be recovered. In general, the liquid should have a boiling point as described above at about 100° C. at 15 mm Hg. With liquids having lower boiling points, an excessive quantity of liquid is removed with the product and must be separated by fractionation or similar techniques. Higher boiling point liquids do not adequately flush or purge the product from the distillation equipment.

The concentration of the high boiling, water-immiscible liquid can range from about 0.1 to about 1 parts/part of the dialkylchlorothiophosphazene compound in the crude reaction mixture. A more preferred concentration is from 10 to 20 weight percent. In general, it is preferred to use as low a concentration as is possible while still maintaining a fluid system under processing conditions. This is particularly true when it is desired to dispose of the fluid residue by burning, using the high boiling liquid as a source of fuel. Higher concentrations can be used although there is no particular advantage from a processing standpoint and actually greater quantities are disadvantageous, due to reduction of product throughput in the recovery equipment and increased costs of using and handling greater volumes of material.

Having described the invention, one skilled in the art could readily envision various changes and modifications thereof which are within the scope of the disclosed process. Therefore, it is desired to limit the invention only by the lawful scope of the following claims.

What is claimed is:

1. In a process for preparing a dialkyl phosphorochloridothioate compound in which phosphorus pentasulfide is reacted with an alcohol selected from saturated alkyl alcohols having from one to about eight carbon atoms and the reaction product is chlorinated to produce the corresponding dialkyl phosphorochloridothioate compound, to convert the sulfur monochloride to free sulfur and separate a majority of the sulfur from the reaction mixture, the improvement comprising distilling said dialkyl phosphorochloridothioate in the presence of from about 0.1 to about 1 part per part of said dialkyl phosphorochloridothioate compound of a hydrocarbon liquid comprising alkyl substituted aromatic hydrocarbons having from 10 to about 30 carbon atoms in which the aromatic hydrocarbon is selected from naphthalene type and anthracene type hydrocarbons.

2. The process of claim 1 in which said dialkyl phosphorochloridothioate is diethyl phosphorochloridothioate.

3. The process of claim 1 in which said dialkyl phosphorochloridothioate is dimethyl phosphorochloridothioate.

4. The process of claim 1 in which said hydrocarbon liquid is a naphthalene.

5. The process of claim 1 in which said hydrocarbon liquid is a naphthalenic oil having a boiling point above about 100° C. at 15 mm Hg.

6. The process of claim 1 in which said hydrocarbon liquid is primarily methylnaphthalene.

7. The process of claim 1 in which said distilling is carried out in the presence of from about 0.1 to about 0.5 parts per part of said dialkylphosphorochloridothioate of said hydrocarbon liquid.

* * * * *